(12) United States Patent
Bhullar

(10) Patent No.: US 7,201,767 B2
(45) Date of Patent: Apr. 10, 2007

(54) DEVICE FOR ULTRAVIOLET RADIATION TREATMENT OF BODY TISSUES

(76) Inventor: Tarseam S. Bhullar, 5820 Ontario Street, Vancouver, British Columbia (CA) V5W 2L7

( * ) Notice: Subject to any disclaimer, the term of this patent is extended or adjusted under 35 U.S.C. 154(b) by 131 days.

(21) Appl. No.: 10/854,190

(22) Filed: May 27, 2004

(65) Prior Publication Data

US 2005/0267551 A1    Dec. 1, 2005

(51) Int. Cl.
*A61N 5/06* (2006.01)
(52) U.S. Cl. .............................. 607/94; 607/88; 607/90
(58) Field of Classification Search ............. 607/90–94
See application file for complete search history.

(56) References Cited

U.S. PATENT DOCUMENTS

| | | | |
|---|---|---|---|
| 4,686,986 A | | 8/1987 | Fenyo et al. |
| 5,344,434 A | | 9/1994 | Talmore |
| 5,582,479 A | * | 12/1996 | Thomas et al. ............. 362/277 |
| 5,647,840 A | | 7/1997 | D'Amelio et al. |
| 5,675,153 A | * | 10/1997 | Snowball ..................... 250/438 |
| 5,758,956 A | * | 6/1998 | Bornhorst et al. .......... 362/294 |
| 5,791,768 A | * | 8/1998 | Splane, Jr. .................. 362/280 |
| 5,855,595 A | | 1/1999 | Fujishima et al. |
| 5,871,522 A | | 2/1999 | Sentilles |
| 6,061,138 A | * | 5/2000 | Gibbons et al. ............. 356/400 |
| 6,157,141 A | * | 12/2000 | Lapatovich et al. ........ 315/248 |
| 6,316,877 B1 | * | 11/2001 | Kaas ........................... 315/56 |
| 6,403,030 B1 | | 6/2002 | Horton, III |
| 6,423,055 B1 | | 7/2002 | Farr et al. |
| 6,447,721 B1 | | 9/2002 | Horton, III et al. |
| 6,491,618 B1 | | 12/2002 | Ganz |
| 6,516,217 B1 | * | 2/2003 | Tsujita ......................... 600/477 |
| 6,524,529 B1 | | 2/2003 | Horton, III |
| 6,580,449 B1 | * | 6/2003 | Meltzer ....................... 348/85 |
| 6,687,534 B2 | * | 2/2004 | Tsujita ......................... 600/476 |
| 6,749,562 B2 | * | 6/2004 | Nakamura et al. .......... 600/181 |
| 2002/0063954 A1 | | 5/2002 | Horton, III |
| 2002/0183729 A1 | | 12/2002 | Parr et al. |
| 2003/0097122 A1 | | 5/2003 | Ganz et al. |
| 2003/0191459 A1 | | 10/2003 | Ganz et al. |
| 2004/0204747 A1 | * | 10/2004 | Kemeny et al. .............. 607/94 |
| 2004/0218858 A1 | * | 11/2004 | Guy ............................. 385/33 |
| 2005/0167611 A1 | * | 8/2005 | Elsegood et al. ........... 250/435 |

FOREIGN PATENT DOCUMENTS

FR    2700211 A1 *  7/1994
GB    2 105 195        3/1983

* cited by examiner

*Primary Examiner*—Henry M Johnson, III
(74) *Attorney, Agent, or Firm*—Richard C. Litman

(57) ABSTRACT

The device for ultraviolet radiation treatment of body tissues includes a UV light source, a halogen light source and a viewing mechanism all connected to a trifurcation joint by fiber optic cables. All three fiber optics cables are bundled together and exit the trifurcation joint and form a flexible shaft having a distal tip. The distal tip is polished to radiate collimated light. The device allows a user to illuminate the target area in or on the human body via the halogen light, to view the target area via the viewing mechanism, and to treat the body tissue via the UV light source. For destroying pathogens the UV light is calibrated to 253.7 nanometers, a germicidal UV wavelength, by selection of a specific light bulb. The UV light source may be a mercury light bulb and it is maintained at a constant wavelength using a fan to regulate the temperature within the UV light housing.

12 Claims, 3 Drawing Sheets

DEVICE FOR ULTRAVIOLET RADIATION TREATMENT OF BODY TISSUES

BACKGROUND OF THE INVENTION

1. Field of the Invention

The present invention relates to ultraviolet (UV) light devices, more particularly to a UV light device that is used to treat body tissues, such as destroying pathogens within the body, eliminating atherosclerotic plaque tissue, treatment of teeth and gums, etc.

2. Description of the Related Art

It is well known that exposing microbes, such as bacteria and viruses, to ultraviolet (UV) light will kill or destroy the entity. The ideal germicidal UV wavelength is 253.7 or 254 nanometers (nm). Microbes are especially sensitive to the effects of ultraviolet light at the 253.7 nm wavelength. Specifically, UV light having a wavelength of 253.7 nm will alter the DNA of the microorganisms, preventing DNA replication and proliferation. Bacteria such as *E. coli* and rotaviruses are made inactive by UV light at the 253.7 nm wavelength. However, not all microbes are affected by the 253.7 nm wavelength. For example, *Cryptosporidium* or *Giardia* requires a different UV intensity and duration of exposure to the particular wavelength. A formula used to describe the UV dosage required to inactivate microbes is:

$$UV\ dosage = UV\ intensity \times exposure\ time.$$

Current devices that kill bacteria on a particular area on the body or that sterilize water, containers or appliances use lasers or UV light. Most devices expose the targeted area with some sort of radiation or phototherapeutic treatment without having provisions for controlling the range of output produced. Other devices dispose the source of the UV light within a patient's body, which carries the risk that the light source may break and cause harm within the body. A device is needed that allows the user to determine the wavelength of the UV output, that can be calibrated to a specific UV wavelength and that can be used safely within the body.

U.S. patent Publication No. 2002/0183729, published on Dec. 5, 2002 and U.S. Pat. No. 6,423,055, issued to Farr et al. on Jul. 23, 2002, disclose a device for delivering radiation or other phototherapeutic treatment to a targeted site. The energy is transmitted through an optical fiber and is projected as an annular light pattern.

U.S. patent Publication No. 2003/0097122, published on May 22, 2003, describes a method and apparatus for treating diseases, such as gum disease and atherosclerotic vascular disease. The apparatus uses visible light, UV light or other light sources, such as lasers, directed through a fiber optic bundle with the light source being located outside the body. The device uses computer logic to control the emission of light in a flashing state.

U.S. patent Publication No. 2003/0191459, published on Oct. 9, 2003, and U.S. Pat. No. 6,491,618, issued on Dec. 10, 2002 to Ganz, disclose an apparatus and method for killing microorganisms within the body, specifically the stomach, using a light radiation source. The apparatus comprises a shaft, a distal radiation distribution head, an optional inflatable balloon, and a light source disposed at the distal tip of the shaft, such as an x-ray device or UV radiation. The instrument can be inserted into the body alone or, if desired, through the lumen of an endoscope. The lamp is disposed within the shaft, as are a spray nozzle, illumination ports, and a viewing port. The lamp may be withdrawn and extended outside the shaft and may be surrounded by an optional inflatable balloon, or a tubular quartz enclosure screen. In a second embodiment, the instrument comprises a control head, a shaft, an external light source and a radiation source. The second embodiment may also use filters to control the wavelength emitted from the device. Both embodiments, however, use a computer to control the power supply and to cause the emitted light to flash intermittently.

U.S. Pat. No. 5,344,434, issued to Talmore on Sep. 6, 1994, discloses an apparatus for photodynamic therapy treatment comprising a lamp possessing a narrow beam of light, a glass lens, a high-pass filter and a light guide. U.S. Pat. No. 5,855,595, issued to Fujishima et al. on Jan. 5, 1999, discloses an apparatus that emits a continuous light spectrum of UV, visible and infrared radiation to treat tumors. The apparatus includes filters and a system for transmitting a beam of light through the filters onto an affected area.

U.S. Pat. No. 5,871,522, issued to Sentilles on Feb. 16, 1999, discloses an apparatus and method for projecting germicidal UV radiation on a target area of the body. The apparatus comprises a reflector having an axis of reflection, a lamp having a wavelength in the UV C range and no radiation in the UV A and B ranges and a collimator made up of a plurality of plates aligned with the axis of reflection for accurate aiming of the condensed radiation beam. U.S. Pat. No. 4,686,986, issued to Fenyo et al. on Aug. 18, 1987, discloses a method and apparatus for promoting healing. The apparatus comprises a light source, having a wavelength exceeding 300 nm, a deflector, and a polarizer.

British Patent Number 2,105,195, published on Mar. 23, 1993, describes an apparatus for stimulating biological processes related to cellular activity with light. The apparatus is meant to promote the healing of lesions on the body surface, such as wounds, ulcers and epithelial injuries. The apparatus comprises a light source emitting light having a wavelength of 300 nm, a fan, a deflecting system and a plurality of light filters.

U.S. Pat. No. 5,647,840, issued to D'Amelio et al. on Jul. 15, 1997, discloses an endoscope having a distally heated distal lens for performing laparoscopic surgery. The endoscope has a fiber optic bundle and may include a fluid flow channel for directing fluid flow across the distal lens.

U.S. Pat. No. 6,403,030, issued on Jun. 11, 2002, and U.S. Pat. No. 6,447,721 issued on Sep. 10, 2002, both to Horton III., describe an ultraviolet wastewater disinfection system and method for treating containers. The system positions a UV light source in a number of ways outside a fluid within the container. The system comprises a housing containing at least one light source, a power source for producing a UV light output and at least one optical component disposed between the light source and the UV light output.

U.S. Pat. No. 6,524,529, issued to Horton III. on Feb. 25, 2003, discloses an ultraviolet disinfection system for treating appliances. The system comprises at least one UV light-ready appliance, at least one light source, a portal for receiving UV light from the light source and a connector disposed at the portal for providing a focused, controlled UV light output. U.S. patent Publication No. 2002/0063954, published on May 30, 2002, describes a portal-based system for ultraviolet sterilization of containers and appliances.

None of the above inventions and patents, taken either singly or in combination, is seen to describe the instant invention as claimed. Thus, a device to destroy pathogens solving the aforementioned problems is desired.

SUMMARY OF THE INVENTION

The device for ultraviolet radiation treatment of body tissues of the present invention comprises a UV light source, a halogen light source, and a viewing mechanism all connected to a trifurcation joint by fiber optic cables. All three fiber optics cables are bundles and exit the trifurcation joint to form a shaft having a distal tip. The distal tip is polished to radiate collimated light. The device allows a user to illuminate the target area in or on the body via the halogen light, to view the target area via the viewing mechanism, and to destroy pathogens via the UV light source. Ideally the UV light is calibrated to 253.7 nanometers, a germicidal UV wavelength, by selection of a specific light bulb. The UV light source may be a mercury light bulb and is maintained at a constant wavelength using a fan to regulate the temperature of the bulb.

These and other features of the present invention will become readily apparent upon consideration of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
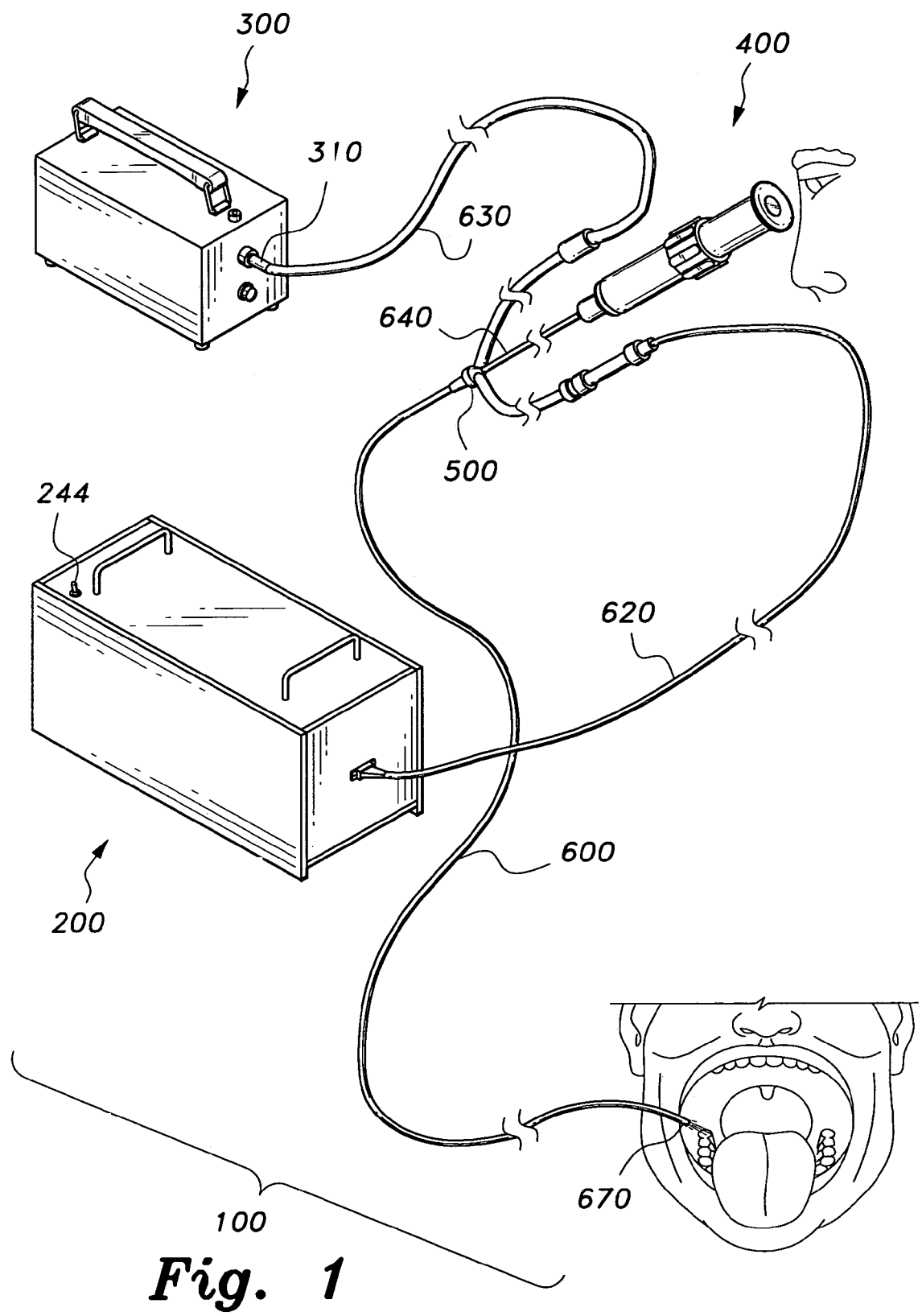
FIG. 1 is an environmental, perspective view of a device to destroy pathogens according to the present invention.

The present invention is a device to kill pathogens, designated generally as 100 in the drawings. As shown in FIG. 1, the device 100 comprises a UV light source 200, a visible (white or halogen light) source 300, a viewing mechanism 400 and fiber optic cables 620, 630, 640 joined into a bundle of fiber optic cables at trifurcation joint 500. A flexible shaft 600, having a first end and a second end is connected to the trifurcation joint 500. The first end of shaft 600 is connected to the trifurcation joint 500, and the second end of shaft 600 defines a distal tip 670. The shaft 600 retains each of the fiber optic cables 620, 630, 640 in a bundle.

The device 100 uses a UV light source 200, preferably the UV being radiated from an incandescent mercury vapor light bulb that is calibrated to emit radiation at a pre-determined wavelength frequency, such as 253.7 nm, or any other wavelength in the UV range of the electromagnetic spectrum. Other bulbs may be used such as an incandescent xenon bulb or similar bulbs. For example, the device 100 may use bulbs generating UV radiation having lower wavelengths for treating sensitive areas in the body, such as the heart, for treating tumors within the body cavity, or for immobilizing microbes that require a different wavelength of radiation than the preferred 253.7 nm, such as *Cryptosporidium* or *Giardia* protozoan parasites affecting the gastrointestinal tract.

Figure 2:
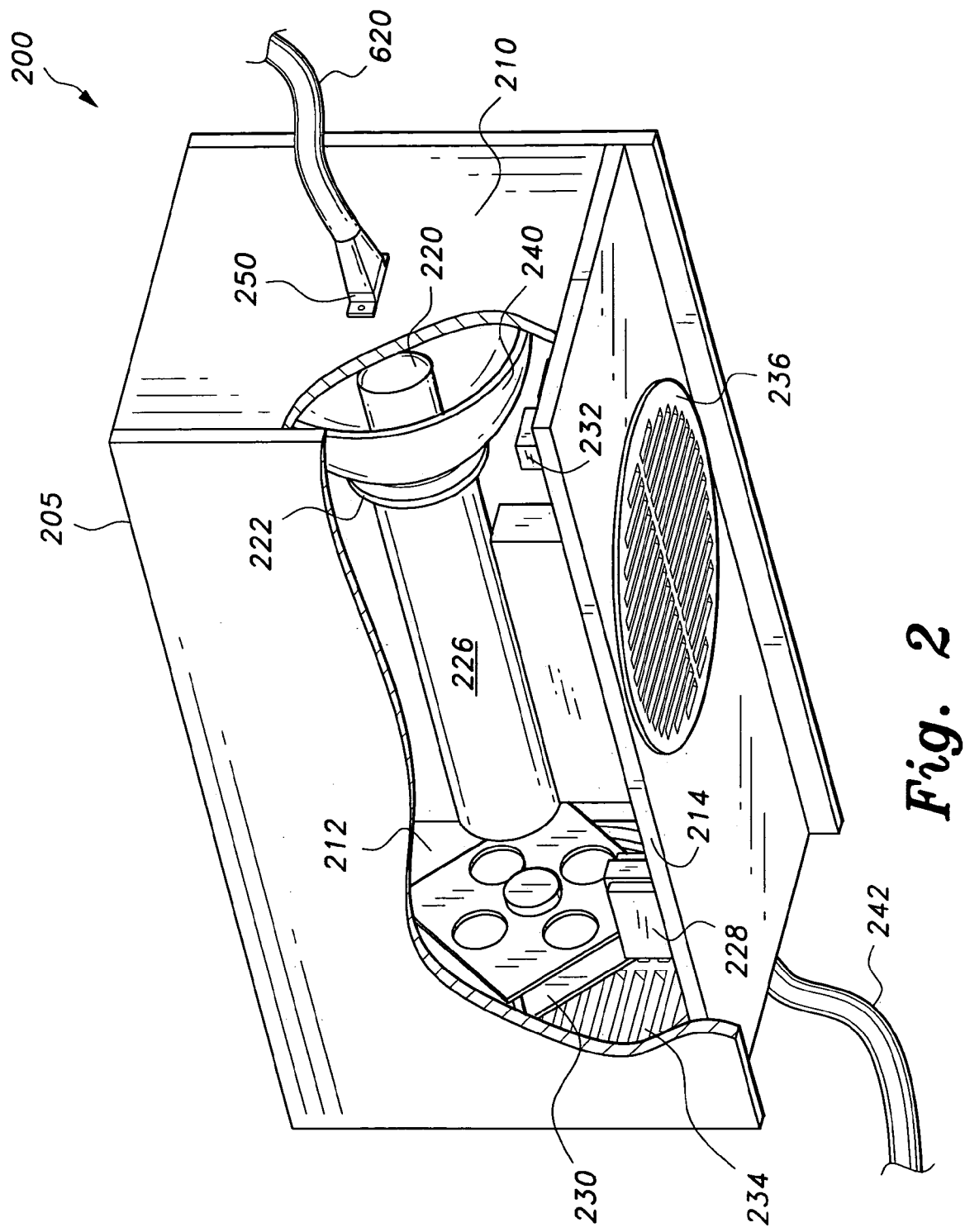
FIG. 2 is a perspective view of the UV light source of the device of the present invention, the housing being broken away and partially in section to show details of the light source.

Referring to FIG. 2, the UV light source 200, also referred to as a UV light projector, includes a housing 205, preferably made of one-quarter inch thick aluminum sheet metal, having a base or floor 214, a front case panel 210, a rear case panel 212 a pair of opposing side panels, and a top panel, the panels and floor comprising six separate sheets joined by stainless steel screws to form the housing 205. The entire housing 205 is preferably anodized both internally and externally to prevent corrosion.

The housing 205 encloses a UV light bulb 220, a threaded reflector 240, a fan 230, a temperature sensor 232, a ballast transformer 228 and an intermediate socket 226. The bulb 220 is screwed into the intermediate socket 226 that is mounted on the floor 214. The reflector 240 shrouds the bulb 220 and targets the UV light into an external portal 250 disposed on the front case panel 210.

The reflector 240 is elliptical in shape, which is a suitable design to capture UV light generated by the bulb 220 and direct it into the external portal 250. The portal 250 possesses a fiber optic connector or coupler to which the fiber optic cable 620 is attached. The coupler joins the fiber optic cable 620 to the housing 205 and focuses light through the cable 620. A lock ring 222 is disposed to the rear of the reflector 240. By unlocking the ring 222 and moving the reflector 240 to or away from the portal 250, UV light may be finely targeted into the fiber optic cable 620 via the coupler disposed within the portal 250.

The projector 200 runs on 110 Volts of alternating current (AC), which is provided through a power cable 242. The power is directed to the ballast transformer 228, which provides the proper voltage for the bulb 220. Electrical wires interconnect the elements of the projector 200 and supply power. An on/off switch 244 is provided for selectively applying power to the UV light source 200.

Fan 230 and temperature sensor 232 are provided for regulation of the temperature within housing 205 in order to maintain the UV radiation at the desired wavelength. The fan 230 keeps the temperature of the skin of the bulb 220 stable. The fan 230 keeps the bulb 220 between 40 to 50 degrees centigrade, the optimal temperature within which the desired UV wavelength output is reached to destroy pathogens. The fan 230 cooperates with the sensor 232 to detect whether the skin temperature of the bulb is outside the optimal temperature range and therefore maintains the radiation wavelength at a constant frequency. When the bulb 220 is outside the optimal temperature range, i.e., too hot, the sensor 232 actuates the fan 230 to turn on and take in cooler air via an intake vent 234. A second vent 236 disposed on the housing 205 permits air to circulate and push out the warm air. Once the bulb 220 is within the optimal temperature range, the fan 230 automatically turns off.

Referring back to FIG. 1, the visible light source 300 houses a halogen light from which white light between about 600 nm to about 400 nm is emitted. The visible light source 300 connects to the fiber optic cable 630 by a coupler 310. The halogen assembly 300, like the projector 200, also operates on AC power. The visible light source 300, as well as the trifurcation joint 500, is commercially purchased from a fiber optic supplier, such as Myriad Fiber Imaging Tech, Inc. of Dudley, Mass. The viewing mechanism 400 is ideally a telescopic eyepiece or endoscope and may also be commercially purchased.

Figure 3:
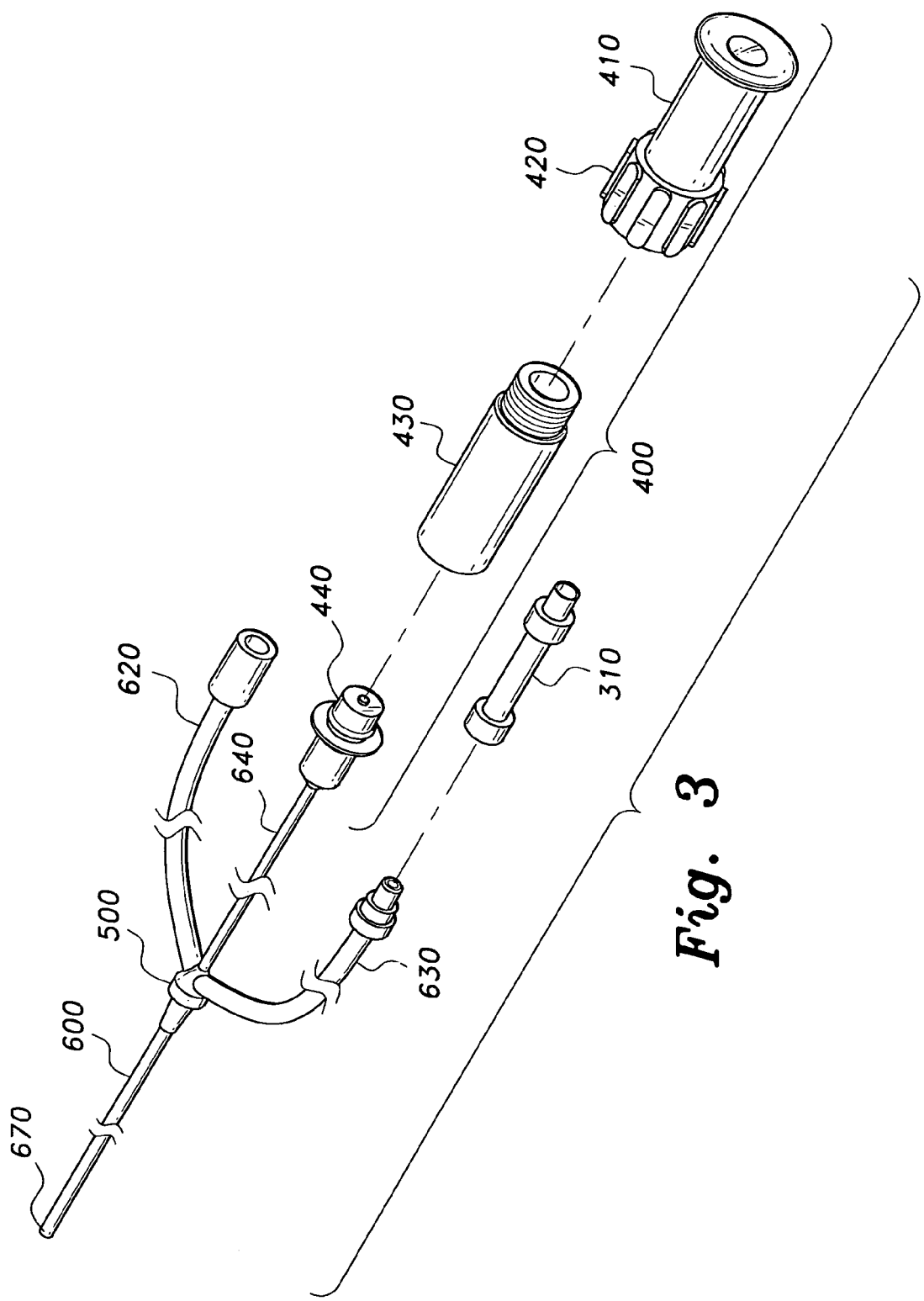
FIG. 3 is an exploded, perspective view of the eyepiece of the device of the present invention.

As shown in FIG. 3, the viewing mechanism 400 comprises a viewing lens or eyepiece 410, a focus ring 420 to adjust the focus of the eyepiece 410, and a coupler 430 disposed between the eyepiece 410 and a proximal end 440 to which the fiber optic cable 640 is attached.

The fiber optic cable 620, which joins the UV light source 200 to the trifurcation joint 500 is made of quartz. Quartz is the optimal type of fiber optic used in the transmittal of UV radiation. Fiber optic cable 620 may comprise a plurality of individual quartz fiber optics. The trifurcation joint 500, which is made of plastic, also receives the two other fiber optic cables 630, 640 from the visible light source 300 and the viewing mechanism 400, respectively. The fiber optic cable 630 between the visible light source 300 and the trifurcation joint 500 is made of borosilicate, while the fiber optic cable 640 between the viewing mechanism 400 and the trifurcation joint 500 is made of an imaging fiber optic.

All three fiber optic cable 620, 630, 640 pass through the trifurcation joint 500 and bundled together to extend down the flexible shaft 600, with each end being disposed at the distal tip 670. The shaft 600 is preferably about four feet long and between about 2 mm to about 5 mm thick, but can be shorter or longer and thicker or thinner. The shaft 600 of the device 100 supplies white light through cable 630 to guide the shaft through the human body and illuminate the target area. The shaft 600 also simultaneously permits the user to view the target area using the imaging cable 640, and permits UV light to radiate from the quartz cable 620 to kill pathogens or clear arterial blockage once the distal tip 670 is properly positioned. The distal tip 670 is flat, and specifically is a plano surface which is polished so that light is collimated as it exits the tip 670. If the tip is not polished then little light will come through.

Being a medical tool, device 100 can be used either internally or externally as a diagnostic as well as therapeutic device. When the device 100 is used within the body as an endoscope, it should be manipulated by one skilled in the art of using endoscopes. The device 100 can easily be inserted into the internal body cavities for use in the lungs, the heart or any other cavity where tumors or pathogens reside. The device 100 can be calibrated at any wavelength based on the type of bulb being used. A higher or lower wavelength bulb can be inserted during calibration. Calibration of the device 100 is desired in carrying out specific procedures. For instance, a lower wavelength frequency is required when the device 100 is used to treat clogged arteries or destroy tumors within the body.

When using the device 100 to clear clogged arteries in the heart, the heart is mapped and then a balloon catheter must be placed in the artery and inflated. Immediately afterwards, the distal tip 670 of flexible shaft 600 is inserted in the same opening through with the balloon catheter had been inserted, for example through the groin or the arm, and areas identified with plaque are given a dose of UV light, which vaporizes the plaque. Here, the bulb 220 used with the device 100 has a low wavelength frequency. The length of the exposure is dependent on the size of the blockage to be vaporized or the type of pathogen desired to be killed. Furthermore, in order to target the plaque, the cardiologist can use chromophore-tagged monoclonal antibodies that selectively attach to plaque. The plaque is then identified by the operator looking into the eyepiece and the UV radiation is directed at the plaque, whereupon the plaque vaporizes. A specific formula used to determine the particular wavelength used to inactivate microbes is:

Ultraviolet dosage=Ultraviolet intensity×Exposure time.

The dosage units are measured in mJ/cm$^2$.

The device 100 also is useful externally when used in the mouth to treat cavities or to clear pathogens during root canal surgery. When treating decaying teeth, the distal tip 670 would first be directed onto the tooth using the viewing mechanism 400 and the white light provided by the halogen light assembly 300. Then UV light would be applied to the target for a pre-determined time to destroy any pathogens, see FIG. 1. By using the device to treat decaying teeth, one forgoes the step of having to drill into the tooth. The cavity can then be filled with enamel or any other suitable filling material, if necessary.

The device 100 is designed for repeated use. This is achieved by decoupling the cables 620, 630, 640 from the visible light source 300 and the UV light source 200, and sterilizing the fiber optic cables 620, 630, 640, and the viewing mechanism 400 by bathing in chemicals, such as steris, cidex, sterrad or ethylene-oxide gas. Autoclaving is not suitable as a sterilization method. Thus, the device 100 and its parts are re-usable once it is sterilized.

It is to be understood that the present invention is not limited to the embodiments described above, but encompasses any and all embodiments within the scope of the following claims.

I claim:

1. A device for ultraviolet radiation treatment of body tissue, comprising:

a ultraviolet (UV) light source having a housing, a UV light assembly disposed within the housing capable of emitting ultraviolet light, and a first fiber optic cable extending from the housing, said UV light assembly including a UV light bulb and a threaded reflector disposed behind the UV light bulb, the reflector being elliptical in shape for capturing UV light generated by the UV light bulb and adjustable for focusing the UV light into the first fiber optic cable;

said UV light source further including a ballast transformer for regulating voltage to the UV light assembly and a thermostatically controlled fan and temperature sensor for cooling the UV light assembly in order to maintain emitted UV light at a calibrated wavelength;

a visible light source having a second fiber optic cable extending therefrom;

a viewing mechanism having an optical lens assembly and a third fiber optic cable extending from the optical lens assembly;

a trifurcation joint connected to the first, second, and third fiber optic cables to form a bundle of fiber optic cables at the trifurcation joint; and a flexible shaft having a first end extending from the trifurcation joint and a second end defining a distal tip having a plano-polished surface, the bundle of fiber optic cables extending through the shaft and terminating at the distal tip;

whereby the flexible shaft is adapted for endoscopic insertion into a human body, the distal tip being directed to a target tissue area by the visible light source and viewing mechanism, the target area being irradiated by the ultraviolet light source.

2. The device for ultraviolet radiation treatment of body tissue according to claim 1, wherein the housing of said UV light source is made of anodized aluminum.

3. The device for ultraviolet radiation treatment of body tissue according to claim 1, wherein said UV light assembly further comprises a lock ring rotatably engaging said threaded reflector, the lock ring permitting fine adjustment of the position of said reflector.

4. The device for ultraviolet radiation treatment of body tissue according to claim 1, wherein the UV light assembly comprises an incandescent mercury vapor light bulb.

5. The device for ultraviolet radiation treatment of body tissue according to claim 1, wherein the UV light assembly comprises an incandescent mercury light bulb.

6. The device for ultraviolet radiation treatment of body tissue according to claim 1, wherein the UV light assembly comprises an incandescent xenon light bulb.

7. The device for ultraviolet radiation treatment of body tissue according to claim 1, wherein said visible light source comprises a halogen light assembly.

8. The device for ultraviolet radiation treatment of body tissue according to claim 1, wherein the said visible light source emits white light in a range between about 600 nm to about 400 nm.

9. The device for ultraviolet radiation treatment of body tissue according to claim 1, wherein said first fiber optic cable comprises a quartz cable.

10. The device for ultraviolet radiation treatment of body tissue according to claim 1, wherein said second fiber optic cable is made of borosilicate.

11. The device for ultraviolet radiation treatment of body tissue according to claim 1, wherein the third fiber optic cable is an imaging fiber optic.

12. The device for ultraviolet radiation treatment of body tissue according to claim 1, wherein said first optic cable comprises a plurality of individual quartz fiber optic strands.

* * * * *